(12) United States Patent
Rose

(10) Patent No.: US 6,595,779 B1
(45) Date of Patent: Jul. 22, 2003

(54) BEHAVIOR MODIFICATION

(76) Inventor: John Edward Rose, 66 Kings Road, Windsor, Berkshire SL4 2AH (GB)

( * ) Notice: Subject to any disclaimer, the term of this patent is extended or adjusted under 35 U.S.C. 154(b) by 0 days.

(21) Appl. No.: 10/019,761

(22) PCT Filed: Apr. 6, 2000

(86) PCT No.: PCT/GB00/01297
§ 371 (c)(1),
(2), (4) Date: Oct. 18, 2001

(87) PCT Pub. No.: WO00/64523
PCT Pub. Date: Nov. 2, 2000

(30) Foreign Application Priority Data

Apr. 21, 1999 (GB) .............................................. 9908983

(51) Int. Cl.[7] .............................................. G09B 19/00
(52) U.S. Cl. ...................................................... 434/236
(58) Field of Search ................................ 434/236, 237, 434/238, 308, 309

(56) References Cited

U.S. PATENT DOCUMENTS

| | | | | |
|---|---|---|---|---|
| 5,217,379 A | * | 6/1993 | Kirschenbaum et al. | 434/236 |
| 5,425,699 A | * | 6/1995 | Speigel | 600/26 |
| 5,719,780 A | * | 2/1998 | Holmes et al. | 700/231 |
| 5,807,114 A | * | 9/1998 | Hodges et al. | 434/236 |
| 5,823,932 A | * | 10/1998 | Speigel | 600/26 |
| 6,081,742 A | * | 6/2000 | Amano et al. | 600/513 |
| 6,139,324 A | * | 10/2000 | Roy et al. | 434/55 |

* cited by examiner

Primary Examiner—John Edmund Rovnak
(74) Attorney, Agent, or Firm—Smith-Hill and Bedell

(57) ABSTRACT

A device is housed in a housing in the general form of a wrist watch. A vibrator within the device can be manually actuated to provide tactile stimulation to the wearer. The device also incorporates a store for storing an audible message available to the wearer, through a headphone socket, loudspeaker or the like, when play back is initiated by a control. During play back, a link device monitors the message being reproduced, and causes activation of the vibrator at appropriate points within the message, as required for effective behaviour modification.

13 Claims, 1 Drawing Sheet

BEHAVIOR MODIFICATION

The present invention relates to behaviour modification and the like in human subjects, and particularly, but not exclusively, to performance enhancement.

There are many situations in which the enhancement of human performance is important or desirable. For instance, many sportsmen wish to be able to enhance their performance in order to achieve greater success, but without making use of performance-enhancing drugs or other artificial aids which would infringe rules applicable to their sport or activity. Other desirable types of behaviour modification include overcoming phobias, fear, stress, road rage, insomnia, hypochondria and the like, and the ability to improve performance by generating positive thoughts when necessary. The present invention may also be used in relation to weight control, rejuvenation, strengthening one's immune system, and the like.

The present invention seeks to provide apparatus which facilitates behaviour modification.

The invention provides a device comprising control means operable, in use, to monitor a recorded message being played to a human subject, and actuator means operable to provide a perceptible stimulation to the human subject, the control means being further operable, at least selectively, to activate the actuator means at a predetermined point or points in the message.

Preferably the control means are further operable to activate the, upon command by the human subject.

Preferably the device further comprises storage means operable to reproduce a recorded message, the storage means may be operable to receive a message for storage and subsequent reproduction. Preferably the storage means is operable to receive a message downloaded from a remote location. The message may be downloaded by means of a global network. The message may be downloaded by wireless means.

The recorded message is preferably an audio message. The device may comprise an output transducer or output port through which a human subject may listen to the message.

Preferably the device is arranged to be worn by the subject. The device may be arranged to be wrist-borne.

The actuator means is preferably operable to provide stimulation which is tactile, audible, visual or by means of smell. The stimulation is preferably by vibration.

Figure 1:
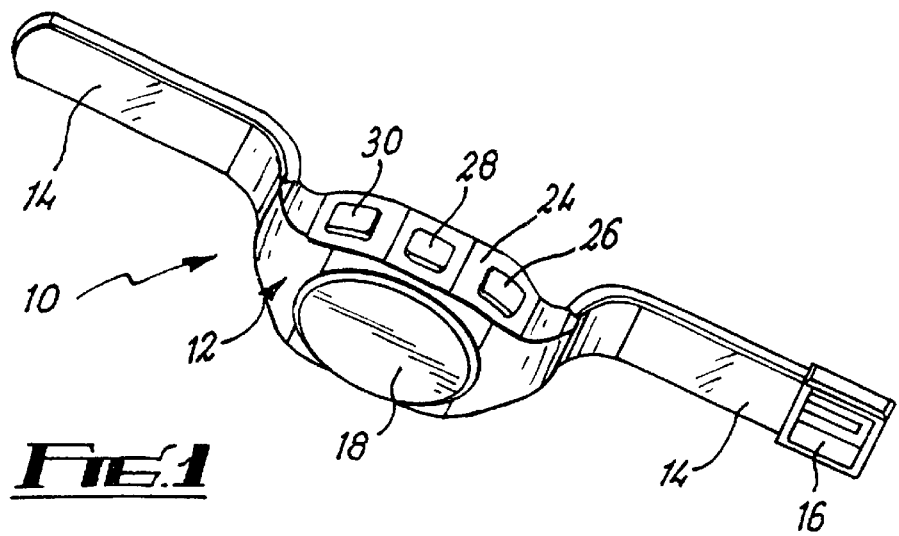
Figure 2:
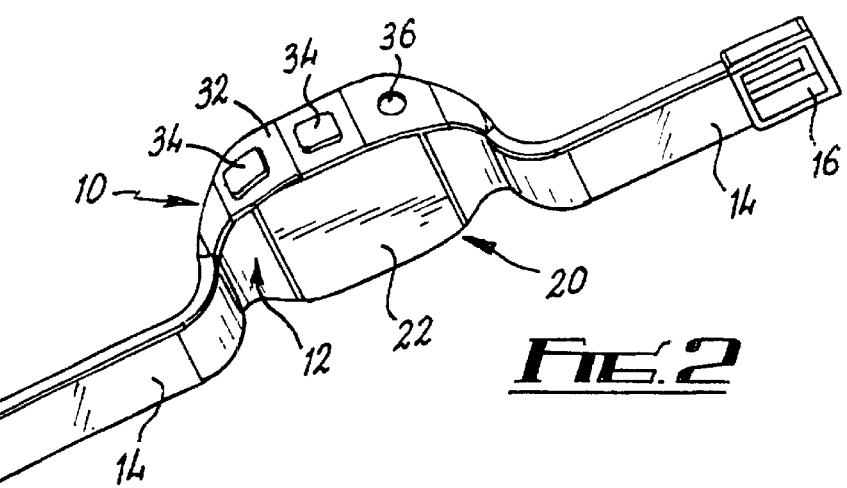
Figure 3:
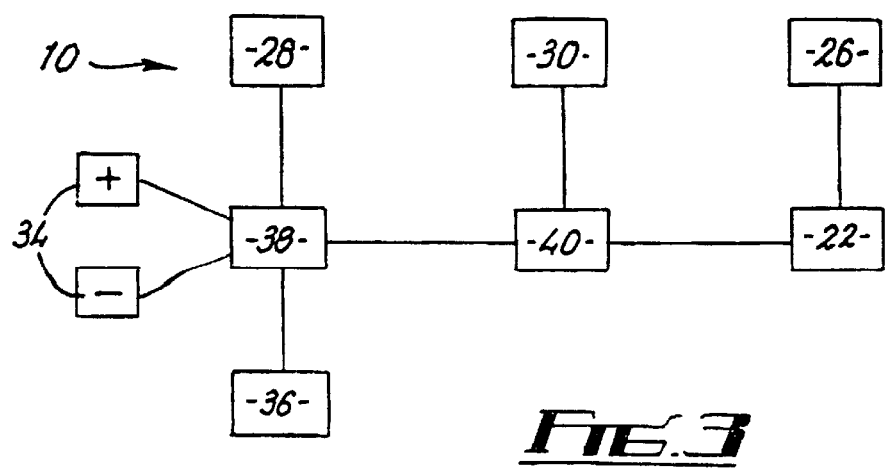

Examples of the present invention will now be described in more detail, by way of example, and by reference to the accompanying drawings, in which:

FIGS. 1 and 2 are schematic perspective views of a device according to the invention, from above and below, respectively; and FIG. 3 is a highly schematic and simplified block diagram of the internal construction of the device of FIGS. 1 and 2.

FIG. 1 shows a device 10 according to the present invention and having the general form of a wristwatch, comprising a main body indicated generally at 12, and straps 14 by means of which the main body 12 may be strapped to the wrist of a user. A buckle 16 or other attachment arrangement is provided for connection of the free ends of the straps 14.

The main body 12 has a front face 18 which may carry brand identification, decorative material or the like, and a rear face 20 which incorporates a vibrating pad 22, as will be described. It will be readily apparent that when the device 10 is wrist-borne, the vibrating pad 22 will be adjacent the wearer's wrist, so that the vibrations can be sensed as tactile stimulation of the wearer's wrist.

A first side wall 24 of the main body 12 incorporates three operator controls, whose purpose will be described in more detail below, and which may be briefly described as a manual buzzer activator 26, a play back activator 28 and an auto/manual switch 30. The other side wall 32 carries two volume control buttons 34 by means of which the volume of audio play-back can be increased or decreased, respectively. The side wall 32 also provides access to an earphone socket 36.

FIGS. 1 and 2 show the general arrangement of the various components. Their functional arrangement, and that of the components within the main body 12, are illustrated schematically in FIG. 3.

In addition to components described above, FIG. 3 shows a storage means 38 and a link circuit 40 connected between the store 38 and the vibrating pad 22, and to the auto/manual switch 30.

The store 38 is a storage device which stores a recorded message and can, upon activation, reproduce the message. The store 38 is preferably a solid state device. Preferably, the message will be an audio message supplied to the user by means of the earphone socket 36 to which the store 38 is connected, so that the user can listen to the message by connecting headphones to the socket 36. The volume of the message heard by the user can be controlled by means of the buttons 34. Alternatively, the device 10 could incorporate a transducer, such as a loudspeaker, to allow the recorded audio message to be heard without the use of headphones.

Alternatively, the recorded message could incorporate or consist of video images in which case, an appropriate output or display device would be incorporated in the device 10.

The recorded message, whether audio or video, is preferably a visualisation programme of the type described in my International Patent Application WO 98/02200. A visualisation programme of the type described therein takes the user through a series of steps in which the desired enhancement is visualised, and an anchor stimulus is taught to the user so that subsequently, perception of that stimulus triggers the visualisation of the desired enhancement, and thus facilitates achievement of the enhancement. The enhancement could relate to performance enhancement in a sport or skill, to overcome the effects of phobias, stress, fear, road rage, insomnia, hypochondria, or the like, to the generation of positive thoughts, or to deal with weight control, feeling and looking younger, strengthening the immune system, and the like.

A visualisation programme of the type taught by my International Patent Application WO 98/02200 requires the user to experience the anchor during the visualisation programme, and for the user to be able to activate the anchor at will thereafter, so that the anchored benefits can be achieved.

The device 10 provides for an anchor in the form of vibration created by the vibrating pad 22.

The device 10 incorporates the activator 28, in the form of a push button, which activates the store 38 to reproduce the recorded message. In a simple form of the device, the store 38 will incorporate only the visualisation programme or may incorporate more than one programme, such as an initial visualisation programme, and another programme to be used subsequently to refresh the effects of the visualisation programme. The form of the activator 28 can be selected according to the number and type of recordings stored in the storage means 38. Alternatively, different instructions could be given by different sequences of operation of the actuator 28. For instance, a single activation of a switch could be used to instruct play-back of the main recorded visualisation programme, whereas operation twice in quick succession could be used to instruct play-back of a refresher programme.

The visualisation programme will require activation of the vibrating pad 22 during the programme, as has been explained above, to create the required anchor. Operation of the vibrating pad 22 is also required subsequently, to re-create the anchor. The vibrating pad 22 can be activated either by the activator 26, or by operation of the link 40, as follows.

Manual operation of the activator switch 26 will cause the vibrating pad 22 to vibrate for a predetermined period of time, such as four seconds. This mode of activation is used to re-create the anchor after the visualisation programme has been used by the user. With the device 10 worn on the wrist, the activator 26 is depressed whenever the user wishes to use the anchor to re-create the benefits of the visualisation programme. The pad 22 is then caused to vibrate, the user senses the presence of the anchor, and the visualisation is triggered.

During the visualisation programme, the user can operate the vibrating pad 22 by operation of the activator 26, as described above and in response to instructions given by the recorded message. Alternatively, the pad 22 can be activated automatically by means of the link 40, connected to the storage means 38 and to the vibrating pad 22. The link 40 is enabled or disabled by the switch 30, which toggles the link "on" or "off". When the link 40 is on, activation signals received from the storage means 38 as part of the recorded message can be passed through to the vibrating pad 22 to activate the pad 22. The activation signals are timed as part of the recorded message, so that the user experiences the anchor at the appropriate point in the recorded message. This provision of automatic actuation of the vibrating pad 22 at the appropriate time in the recorded message ensures that the anchor effect is created reliably, without requiring correct activation of the pad 22 by the user. Alternatively, it may sometimes be desirable (for instance, during a refresher programme) for the user to activate the pad 22. If so, the link 40 can be disabled.

The present invention therefore provides a device which is compact, easy to wear (and thus convenient to wear for long periods of time) and simple to operate.

The scope of the invention is not restricted to the detailed arrangements described above. Alternative arrangements could be used, particularly according to the technologies adopted for implementing the various components. For instance, the storage means 38 could be omitted, there being provided a connection by which a signal can be received from a remote source, either by wireless means such as a mobile telephone, or through connection to the Internet, or from the Internet by connection via a mobile phone (such as in WAP (Wireless Access Protocol) format), or by another alternative technique. In this possibility, the message would be stored at the remote location, such as on an appropriate web-site, for downloading and reproduction as required. In this alternative, the link 40 would be used to detect activation signals within the message being downloaded, in the same manner as has been described in relation to a message being reproduced from the storage means 38.

In a further alternative, messages could be downloaded from a remote location, as just described, but then stored within the device, rather than being immediately reproduced. In this alternative, the storage means 38 would again be required. Having been stored in this way, the downloaded message is then available for use in the manner described above in relation to the drawings. It is envisaged that many different technologies could be used for a writeable memory to be used in this way, which could be in the recently released MP3 format. Thus, the device can be supplied to the user initially without any message within the storage means 38, the user then being required to access a selected message (such as a message relating to a particular program or for dealing with a particular problem); download that message to the storage means for storage thereafter, and then to operate the device in the manner described above, to reproduce the recorded message now stored within the device, to which the link will respond to activate the vibrating pad, as required.

Connections to a remote location could be achieved by means of the Internet or other global communication network. For convenience, it may be appropriate to provide for downloading via a mobile phone, such as by means of the WAP (Wireless Access Protocol) format.

In a further alternative, a user could make use of an existing storage device, not forming part of the device 10, such as an existing tape recorder, solid state recorder, MP3 recorder or the like, so that a visualisation program can be downloaded, stored in the existing device, and then reproduced by that device, at which stage the link will operate as previously described.

The pad 22 could provide an alternative form of perceptible stimulation, such as heat, visual or smell stimulation. The location of the device 22 within the device 10 will be chosen according to the nature of the stimulation to be provided.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

What is claimed is:

1. A device comprising control means operable, in use, to monitor a recorded message being played to a human subject, and actuator means being operable in use to respond to an activation signal within said message to provide a perceptible stimulation to the human subject wherein the control means is further individually operable, at least selectively by the human subject, to activate the actuator means at a predetermined point or points in the message independently of the activation signal within said message.

2. A device according to claim 1, wherein the control means are further operable to activate the actuator means alone upon command by the human subject.

3. Apparatus according to claim 1, wherein the device further comprises storage means operable to reproduce a recorded message.

4. A device according to claim 3, wherein the storage means is operable to receive a message for storage and subsequent reproduction.

5. A device according to claim 4, wherein the storage means is operable to receive a message downloaded from a remote location.

6. A device according to claim 5, wherein the storage means is operable to download by means of a global network.

7. A device according to claim 5, wherein the storage means is operable to download by wireless means.

8. A device according to claim 1, wherein the recorded message is an audio message.

9. A device according to claim 1, comprising an output transducer or output port through which a human subject may listen to the message.

10. A device according to claim 1 and arranged to be worn by the subject.

11. A device according to claim 10, and arranged to be wrist-borne.

12. A device according to claim 1, wherein the actuator means is operable to provide stimulation which is tactile, audible, visual or by means of smell.

13. A device according to claim 12, wherein the stimulation is by vibration.

* * * * *